USO07186850B2

(12) United States Patent
Silverberg

(10) Patent No.: US 7,186,850 B2
(45) Date of Patent: Mar. 6, 2007

(54) SYNTHESIS OF CANNABINOIDS

(75) Inventor: Lee Jonathan Silverberg, Cherry Hill, NJ (US)

(73) Assignee: Johnson Matthey Public Limited Company, London (GB)

( * ) Notice: Subject to any disclaimer, the term of this patent is extended or adjusted under 35 U.S.C. 154(b) by 263 days.

(21) Appl. No.: 10/479,021

(22) PCT Filed: May 9, 2002

(86) PCT No.: PCT/GB02/02159

§ 371 (c)(1),
(2), (4) Date: Aug. 5, 2004

(87) PCT Pub. No.: WO02/096899

PCT Pub. Date: Dec. 5, 2002

(65) Prior Publication Data

US 2004/0249174 A1    Dec. 9, 2004

(30) Foreign Application Priority Data

May 25, 2001  (GB) ................................. 01127521

(51) Int. Cl.
*C07D 311/78* (2006.01)
*C07D 311/94* (2006.01)
(52) U.S. Cl. ...................... 549/381; 549/385; 549/388
(58) Field of Classification Search ............... 549/381, 549/385, 388
See application file for complete search history.

(56) References Cited

U.S. PATENT DOCUMENTS 5,227,537 A    7/1993 Stoss et al.

FOREIGN PATENT DOCUMENTS

EP    0 494 665 A1    7/1992

OTHER PUBLICATIONS

Handrick et al., Hashish: Synthesis of (-)-Δ9-tetrahydrocannabinol (THC) and its biologically potent metabolite 3'-hydroxy- Δ9-THC, Tetrahedron Lett., No. 8, pp. 681-684 (1979).*
Raj K. Razdan, "The Total Synthesis of Cannabinoids" in *The Total Synthesis of Natural Products*, vol. 4, ed. John ApSimon (Wiley, Apr. 1981), pp. 239-243.
Leslie Crombie, W. Mary L. Crombie, Sally V. Jamieson, and Christopher J. Palmer, "Acid-catalysed Terpenylations of Olivetol in the Synthesis of Cannabinoids," *J. Chem. Soc. Perkin Trans I*, Issue 5, 1998, pp. 1243-1250.
R. W. Rickards, H. Roenneberg, "Synthesis of (−)-Δ$^9$-6a, 10a-tetrahydrocannabinol. Boron trifluoride catalyzed arylation by a homocuprate," *J. Org. Chem.*, vol. 49, No. 3, 1984, pp. 572-573.
Wayne E. Childers, Jr. and Harold W. Pinnick, "A Novel Approach to the Synthesis of Cannabinoids," *J. Org. Chem.*, vol. 49, No. 26, 1984, pp. 5276-5277.
Tetsuji Kametani, Hiroshi Kurobe, and Hideo Nemoto, Stereoselective Cyclization assisted by the Selenyl Group. Biogenetic-type Synthesis of the p-Methane Series, *J. Chem. Soc. Perkin Trans. I*, Issue 3, 1981, pp. 756-760.
G .R. Handrick, D. B. Uliss, H. C. Dalzell and R. K. Razdan, Hashish[1]: Synthesis of (-)-Δ$^9$-Tetrahydrocannabinol (THC) and its Biologically Potent Metabolite 3'-Hydroxy-Δ$^9$-THC, *Tetrahedron Letters*, No. 8, pp. 681-684.
Leslie Crombie, W. Mary L. Crombie, Christopher J. Palmer and Sally V. Jamieson, "Tetrahydrocannabinols by Terpenylation of Olivetol with (+)-trans-2- and -3-Carene Epoxides," *Tetrahedron Letters*, vol. 24, No. 30, 1983, pp. 3129-3132.
International Search Report dated Sep. 9, 2002, from International Application No. PCT/GB02/02159.
British Search Report dated Nov. 27, 2001, from British Application No. 0112752.1.

* cited by examiner

*Primary Examiner*—Kamal Saeed
*Assistant Examiner*—Susannah L. Chung
(74) *Attorney, Agent, or Firm*—RatnerPrestia

(57) ABSTRACT

The present invention relates to a process for the production of compound (A) comprising reacting compound (B) with compound (C). A further ring closure reaction may be necessary. The invention further relates to certain novel compounds of formula (B).

21 Claims, No Drawings

SYNTHESIS OF CANNABINOIDS

This application is the U.S. National Phase application of PCT International Application No. PCT/GB02/02159.

The present invention relates to a novel process that can be used to produce (−)-$\Delta^9$-tetrahydrocannibinol and related cannibinoid compounds. The invention further relates to novel compounds used in the process.

(−)-$\Delta^9$-Tetrahydrocannibinol ($\Delta^9$-THC) is the active ingredient in marijuana. It is used therapeutically as an inhalant or an oral drug for stimulation of appetite among AIDS and cancer chemotherapy patients. Related cannibinoid compounds that show pharmacological activity are also known. In particular, there have been attempts to produce water soluble analogues of $\Delta^9$-THC ('The Total Synthesis of Cannibinoids' in The Total Synthesis of Natural Products, Vol 4, John ApSimon, Wiley, 1981, pp 239–243).

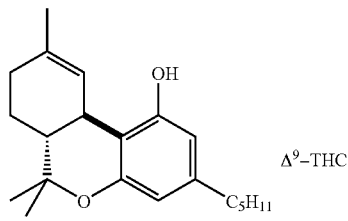

$\Delta^9$-THC

The chemical synthesis and isolation of $\Delta^9$-THC are both challenging. $\Delta^9$-THC is a very high boiling, viscous liquid. It is very prone to acid-catalysed isomerization to the thermodynamically more stable $\Delta^8$ isomer, it is easily oxidized by oxygen to inactive cannibinol, and it is sensitive to light and heat. All of these factors make purification difficult, especially on an industrial scale, and chromatography has generally been used.

Previous syntheses of $\Delta^9$-THC have tended to be either lengthy or low-yielding. Most involve coupling of a chiral terpene to a resorcinol derivative. The primary difficulty has been lack of selectivity in the coupling. Acid catalysed couplings have generally led to mixtures of products (Crombie et al, J Chem Soc. Perkin Trans. I 1988 1243). Attempts to avoid the selectivity problem by using base-catalysed coupling reactions have involved lengthier syntheses overall (Rickards et al, J. Org. Chem. 1984 49 572). Syntheses not using chiral terpenes have yielded racemic product (Childers et al, J. Org. Chem. 1984 49 5276).

In seemingly the best known method (U.S. Pat. No. 5,227,537), Stoss claims that acid-catalysed coupling of (+)-p-menth-2-ene-1,8-diol (1) with olivetol (2) can be stopped at the intermediate Friedel-Crafts product (3), and then the intermediate (3) can be isolated and converted in good yield to $\Delta^9$-THC using $ZnBr_2$ (24 hours, refluxing $CH_2Cl_2$). The present inventors have encountered several problems with this scheme. The initial p-toluenesulfonic acid catalysed Friedel-Crafts reaction was difficult to stop cleanly at the intermediate (3) under Stoss' conditions and gave mixtures of the intermediate (3) and $\Delta^9$-THC, the ring-closed product. Any $\Delta^9$-THC formed is likely to isomerize to $\Delta^8$-THC under the disclosed conditions. The use of a heavy metal such as $ZnBr_2$ in the last step of an industrial process is highly undesirable as it may lead to traces of metal in the product, and this is especially undesirable for pharmaceuticals. Stoss' method therefore appears to offer no real advantage in yield or purity of $\Delta^9$-THC over a one-pot coupling that goes directly to $\Delta^9$-THC. Razdan has published a one-pot method for coupling of (+)-p-menth-2-ene-1,8-diol (1) with olivetol (2) to produce $\Delta^9$-THC (Razdan et al, Tet. Lett. 1983 24 3129). This also suffers from several problems: it uses nearly 14 equivalents of $ZnCl_2$ as the acid, and uses six equivalents of olivetol (2). Even under these conditions, the yield is still only 28% from (+)-p-menth-2-ene-1,8-diol (1).

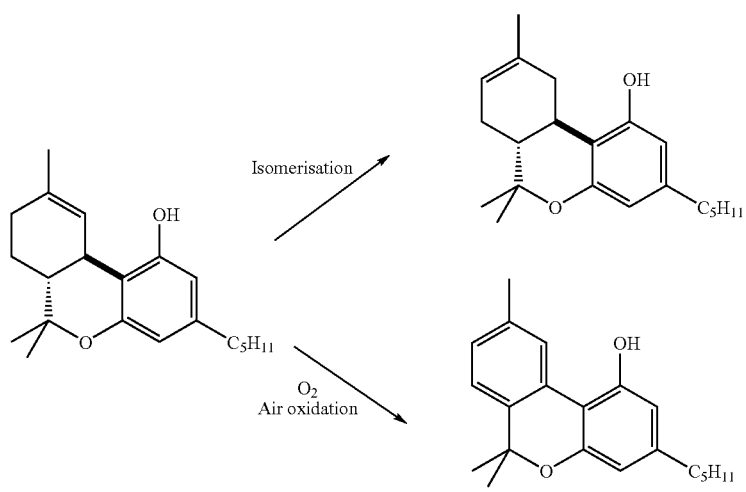

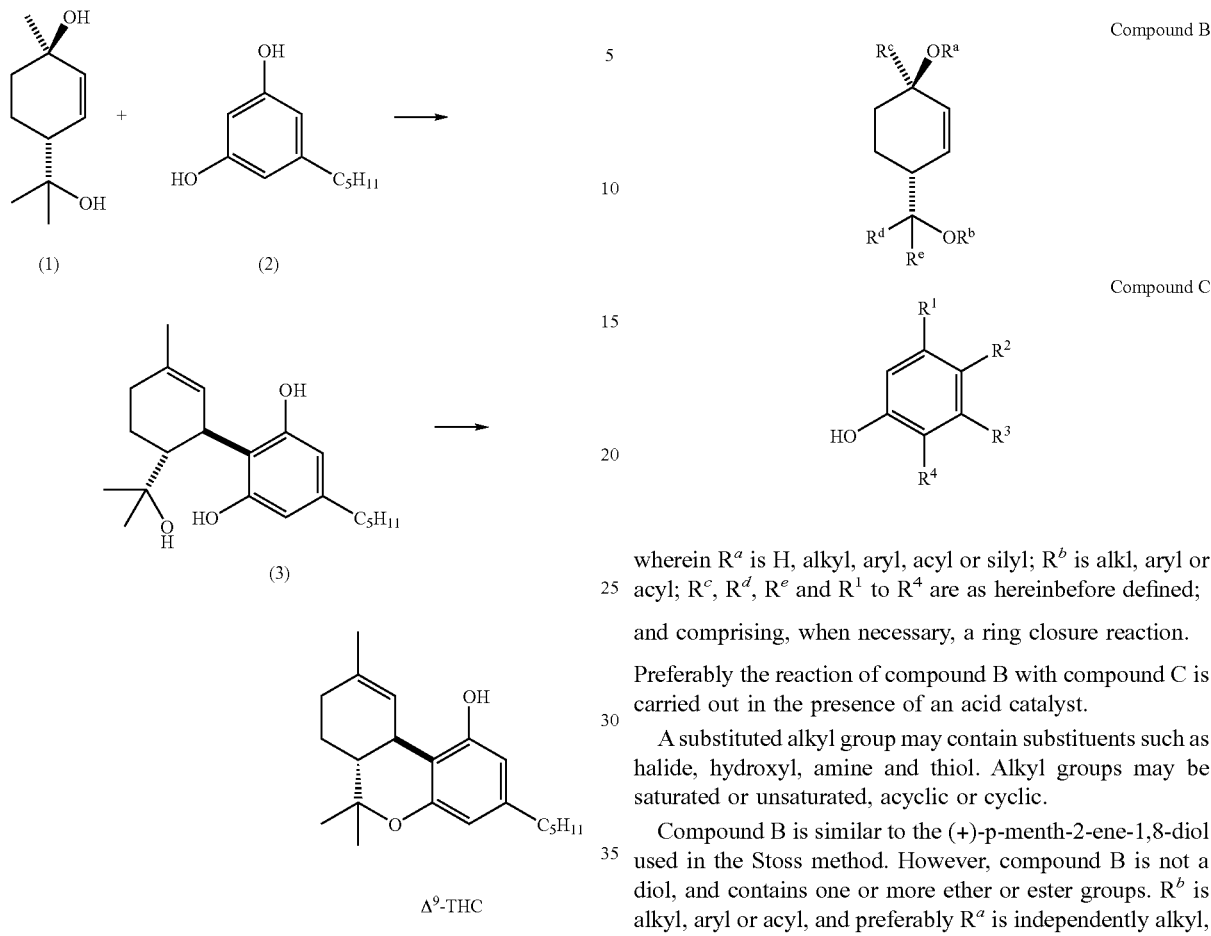

Thus there is a need for a short, practical, high-yielding synthesis of Δ⁹-THC that can be practised on an industrial scale. This is the problem that the present inventors have set out to address.

Accordingly the present invention provides a process for the production of a compound of general formula A:

Compound A

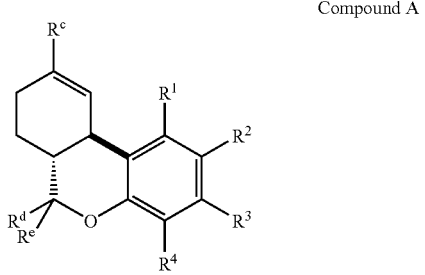

wherein $R^c$, $R^d$ and $R^e$ are independently H, alkyl, or substituted alkyl; and $R^1$ to $R^4$ are independently H, OH, OR' (R' is alkyl, aryl, substituted alkyl or aryl, silyl, acyl, or phosphonate), alkyl, substituted alkyl, aryl, acyl, halide, amine, nitrate, sulphonate or phosphonate;

comprising reacting compound B with compound C:

Compound B

Compound C wherein $R^a$ is H, alkyl, aryl, acyl or silyl; $R^b$ is alkl, aryl or acyl; $R^c$, $R^d$, $R^e$ and $R^1$ to $R^4$ are as hereinbefore defined;

and comprising, when necessary, a ring closure reaction.

Preferably the reaction of compound B with compound C is carried out in the presence of an acid catalyst.

A substituted alkyl group may contain substituents such as halide, hydroxyl, amine and thiol. Alkyl groups may be saturated or unsaturated, acyclic or cyclic.

Compound B is similar to the (+)-p-menth-2-ene-1,8-diol used in the Stoss method. However, compound B is not a diol, and contains one or more ether or ester groups. $R^b$ is alkyl, aryl or acyl, and preferably $R^a$ is independently alkyl, aryl or acyl.

In a preferred embodiment, $R^b$ is acyl, and $OR^b$ is an ester group. Suitable ester groups include acetate, propionate, butyrate, trimethylacetate, phenylacetate, phenoxyacetate, diphenylacetate, benzoate, p-nitrobenzoate, phthalate and succinate.

In an especially preferred embodiment both $R^a$ and $R^b$ are acyl groups so that compound B is a diester. The two ester groups are suitably chosen independently from acetate, propionate, butyrate, trimethylacetate, phenylacetate, phenoxyacetate, diphenylacetate, benzoate, p-nitrobenzoate, phthalate and succinate. An especially preferred compound has $OR^a=OR^b=$diphenylacetate:

(4)

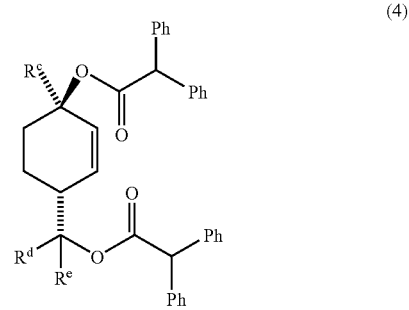

$R^c$, $R^d$ and $R^e$ can be varied independently of $R^a$ and $R^b$ and will affect the structure of the product, compound A. $R^c$ is suitably Me or H, preferably Me. $R^d$ and $R^e$ are suitably Me or $CH_2OH$, preferably Me.

Compound C is a phenolic compound and is preferably a resorcinol derivative such as olivetol (3).

$R^1$ is preferably OR" wherein R" is H, alkyl, substituted alkyl, acyl or silyl. Most preferably $R^1$ is OH.

Preferably, $R^2$ and $R^4$ are H.

$R^3$ is suitably an alkyl group or substituted alkyl group. In a preferred embodiment, $R^3$ is $C_5H_{11}$. $R^3$ may contain groups that promote water solubility, eg ketone, ester, hydroxyl or amine groups. In one embodiment of the invention, $R^3$ contains a thioketal (this can be further converted to an aldehyde).

Most preferably, compound C is olivetol (3), wherein $R^1$ is OH, $R^2$ is H, $R^3$ is $C_5H_{11}$ and $R^4$ is H.

Suitably, one equivalent of compound B is reacted with approximately one equivalent of compound C.

In a preferred embodiment of the invention compound B is an ether or ester of (+)-p-menth-2-ene-1,8-diol ($R^c$=Me, $R^d$=Me, $R^e$=Me), compound C is olivetol ($R^1$=OH, $R^2$=H, $R^3$=$C_5H_{11}$, $R^4$=H) and the product, compound A, is $\Delta^9$-THC.

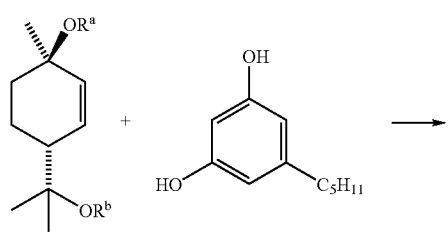

The present invention therefore provides a novel synthesis of $\Delta^9$-THC.

The present invention provides both a one-step and a two-step process for the production of compound A. In the one-step process the reaction of compound B and compound C produces compound A directly. In the one-step process, suitably about one equivalent of acid catalyst is used, eg between 0.8 to 1.5 equivalents. Preferably the reaction is carried out below 0° C., most preferably from −20° C. to 0° C.

In the two-step process the reaction of compound B and compound C produces a ring-opened product, compound D:

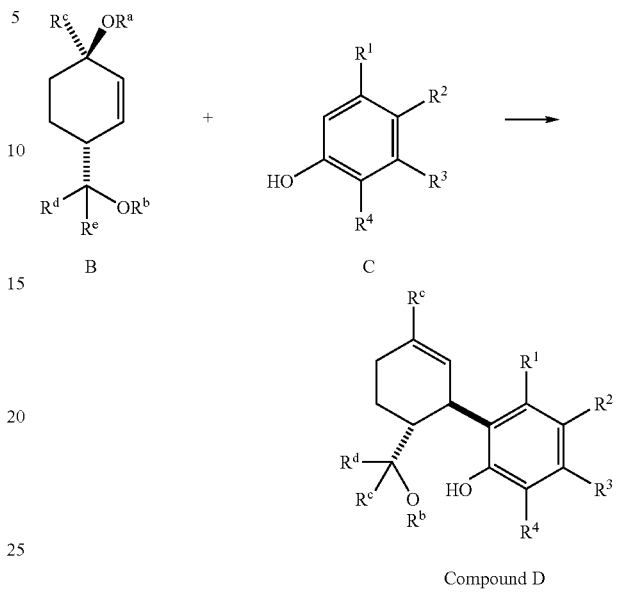

Compound D

For the two-step process, suitably less than one equivalent of acid is used, preferably from 0.1 to 0.5 equivalents. Preferably the reaction is carried out below 0° C., more preferably below −10° C. A ring closure step is then carried out. Suitable reagents for the ring closure step include acids such as $BF_3.(OEt)_2$ or TsOH. One possible advantage of the two-step process is that if compound D is a crystalline solid, purification of the intermediate is straightforward and this may lead to higher purity in the final product, compound A.

The present invention provides one-step and two-step syntheses that can be used to produce $\Delta^9$-THC. The syntheses show improved selectivity and yield compared to prior art methods. The amount of isomers generated is small and purification is simple. The phenolic reactant (compound C) is not used in excess. The process is suitable for scale-up to an industrial process.

Preferably the yield of the synthesis of $\Delta^9$-THC is greater than 50%, more preferably the yield is greater than 75%. The process also provides high purity $\Delta^9$-THC. Preferably $\Delta^9$-THC is obtained in greater than 70% purity, more preferably greater than 90% purity. Methods known in the art can be used to further purify the products of the reaction.

The process of the present invention is suitably carried out in a polar aprotic solvent, preferably methylene chloride.

Suitable acid catalysts include most Lewis acids. Non-metallic catalysts such as $BF_3.OEt_2$ and toluenesulfonic acid are preferred. Non-metallic catalysts offer advantages over the zinc catalysts used in the Stoss and Razdan methods because there is no possibility of a metal residue in the product. $BF_3.OEt_2$ is preferred because it is easily removed from the reaction mixture, and is less prone to causing isomerisation of $\Delta^9$-THC to $\Delta^8$-THC than p-TsOH. Suitably about one equivalent of catalyst or less is used, eg 0.1 to 1.5 equivalents. This offers a clear improvement over Razdan's method where 14 equivalents of acid are used.

Procedures for isolating the product, compound A, from the reaction mixture are well known to those in the art. Chromatography can be used to purify the product.

Certain compounds of structure B are novel and are particularly advantageous when used in the present invention. Compounds wherein both $OR^a$ and $OR^b$ are chosen independently from acetate, propionate, butyrate, trimethylacetate, phenylacetate, phenoxyacetate, diphenylacetate, benzoate, p-nitrobenzoate, phthalate and succinate (provided that only one of $OR^a$ and $OR^b$ is acetate) represent a further aspect of this invention. Preferably the groups are chosen so that compound B is a solid. Preferably both $OR^a$ and $OR^b$ are diphenylacetate. Preferably, $R^c$, $R^d$ and $R^e$ are Me.

Compound B can be produced by a variety of methods. Compounds wherein $R^a$=H or silyl can be prepared by the ring-opening of epoxides (5) with an alcohol, a carboxylic acid or silylated derivatives of alcohols and carboxylic acids. Reactions of this type are described in a co-pending patent application by the present inventors.

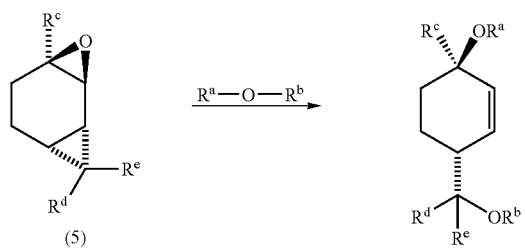

(5)

Compounds wherein $R^a$ and $R^b$ are both the same can be produced by base catalysed reaction of the corresponding diol (6) with anhydrides or chlorides.

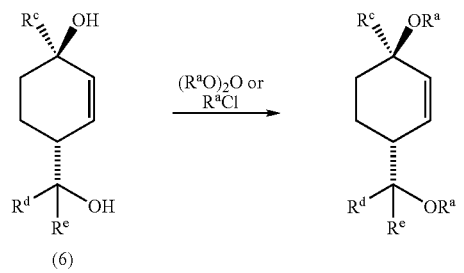

(6)

Compounds wherein $R^a$ is not H or silyl and wherein $R^a$ and $R^b$ are different can be produced by base-catalysed reaction of mono-ethers or mono-esters (7) with ethers or chlorides.

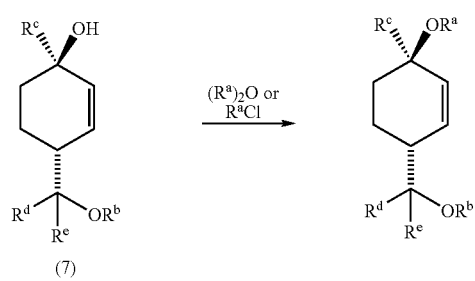

(7)

The following examples are illustrative but not limiting of the invention.

General Experimental Details

Anhydrous solvents were purchased from Aldrich Chemical Company (Milwaukee, Wis., USA). Samples of $\Delta^9$-THC and $\Delta^8$-THC were obtained from RBI/Sigma (Natick, Mass., USA). (+)-p-Menth-2-ene-1,8-diol was prepared as described in a co-pending patent application by the present inventors. TLC plates (silica gel GF, 250 micron, 10×20 cm) were purchased from Analtech (Newark, Del., USA). TLCs were visualized under short wave UV, and then by spraying with ceric ammonium nitrate/sulfuric acid and heating. Column chromatography was carried out using TLC grade silica gel purchased from Aldrich Chemical Company. NMR spectra were obtained on a Bruker 300 MHz instrument. HPLC area percentages reported here are not corrected. HPLCs were run on Shimadzu LC-10AD.

EXAMPLE 1a

One-Step Reaction of bis(diphenylacetate) Compound (4) with Olivetol (3) to Produce $\Delta^9$-THC Preparation of bis(diphenylacetate) Compound (4)

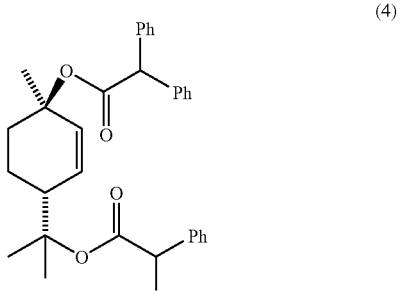

(4)

A 25 ml three-necked roundbottom flask with a stir bar was oven-dried, fitted with septa, and cooled under $N_2$. Pyridine (12 ml) was added and the pale yellow solution was stirred. Diphenylacetyl chloride (5.69 g, 4.2 eq.) was added. The solution turned brown. N,N-dimethylaminopyridine (0.1435 g, 0.2 eq.) was added. The mixture was stirred for 1 hour. (+)-p-Menth-2-ene-1,8-diol (1.00 g) was added. The mixture became a lighter colour and solids precipitated. The slurry was allowed to stir overnight at room temperature. The reaction was quenched with water. The mixture was extracted three times with ethyl acetate. The organics were combined and washed with 2M HCl, saturated $NaHCO_3$, and saturated NaCl (aq.), dried over $Na_2SO_4$, filtered and concentrated in vacuo to orange oil. The oil was dissolved in hot methanol and cooled to crystallize. The white solid was collected and washed twice with cold methanol. After drying under vacuum, the yield was 3.282 g (76.8% yield). $^1$H NMR (CDCl$_3$): δ (ppm) 7.4–7.2 (m, 20H), 5.89–5.84 (dd, 1H), 5.51–5.47 (dd, 1H), 4.90 (s, 2H), 2.7–2.6 (m, 1H), 2.0–1.9 (m, 2H), 1.7–1.6 (m, 1H), 1.43 (s, 3H), 1.42 (s, 3H), 1.40 (s, 3H), 1.35–1.2 (m, 1H). $^{13}$C NMR: δ (ppm) 171.47, 171.44, 139.06, 138.84, 132.38, 128.64, 128.56, 128.51, 128.46, 128.28, 127.11, 127.07, 127.02, 85.12, 80.91, 58.32, 57.86, 44.22, 33.81, 25.41, 23.32, 22.81, 21.41. M.p. 111° C. Elemental Analysis: 81.66% C, 6.59% H. $R_f$ (20% EtOAc/hexane): 0.54. $[\alpha]_D^{25}$=+61.50 (c=1.00, CHCl$_3$). IR (KBr, cm$^{-1}$): 3061, 3028, 1720.5 (carbonyl stretch).

One-Step Reaction

A 25 ml roundbottom flask with a stir bar was oven-dried, fitted with septa, and cooled under $N_2$. The bis(diphenylacetate) (4) (279 mg, 0.499 mmol) and olivetol (90 mg) were added. Anhydrous $CH_2Cl_2$ (8 ml) was added and stirred. The solution was cooled to −5° C. internal temperature. $BF_3 \cdot (OEt)_2$ (64 μl, 1.0 eq.) was added. The solution gradually darkened to orange. After 30 minutes, the reaction was quenched with 10% $Na_2CO_3$ (10 ml). The layers were separated and the organic layer was washed with 2×5 ml 10% $Na_2CO_3$. The aqueous washes were combined and extracted twice with $CH_2Cl_2$. The organics were combined and washed with water and saturated NaCl solution, then dried over $Na_2SO_4$, filtered, and concentrated in vacuo to light yellow oil. The oil was chromatographed on 5 g TLC mesh silica to yield 135.2 mg (86.1%) of $\Delta^9$-THC. NMR did show a small amount of solvent present. HPLC showed 96.6 area percent $\Delta^9$-THC. $^1$H NMR agreed with published reports and commercial samples. $^{13}$C NMR ($CDCl_3$): δ (ppm) 154.81, 154.16, 142.82, 134.41, 123.74, 110.11, 107.54, 77.18, 45.83, 35.47, 33.58, 31.52, 31.17, 30.63, 27.58, 25.03, 23.34, 22.53, 19.28, 13.99. HPLC R.T.: 28.34 min. $R_f$ (10% MTBE/hexane): 0.30. $[\alpha]_D^{25}=-174.2°$ (c=1.16, EtOH).

EXAMPLE 1b

Reaction of bis(diphenylacetate) (4) Compound with Olivetol to Produce Ring-Open Intermediate Bis(diphenylacetate) (4) was prepared as for example 1a.

A 25 ml 2-neck roundbottom flask with a stir bar was oven-dried, fitted with septa, and cooled under $N_2$. Bis(diphenylactetate) (4) (279 mg, 0.499 mmol) and olivetol (90 mg) were added. Anhydrous $CH_2Cl_2$ (8 ml) was added. The solution was stirred to dissolve the solids and then cooled to −20° C. internal temperature. $BF_3 \cdot (OEt)_2$ (16 μl, 0.25 eq.) was added. The solution was stirred for 12 minutes and then quenched with 10% $Na_2CO_3$ (aq.) (6 ml). The mixture was extracted twice with $CH_2Cl_2$. The combined organics were washed with water and saturated NaCl, dried over $Na_2SO_4$, filtered, and concentrated in vacuo to oil. Chromatography on 10 g TLC mesh silica gel (2% MTBE/hexane—15%) yielded $\Delta^9$-THC (fractions 16–22, 31.4 mg, 20.0% yield), but the predominant product was the diphenylacetate triol (the ring open product corresponding to compound D) (fr. 24–37, 160 mg, 60.7% yield). $^1$H NMR ($CDCl_3$): δ (ppm) 7.26–71.8 (m, 10H), 6.26 (br s, 1H), 6.04 (br s, 1H), 5.35 (s, 1H), 4.51 (s, 1H), 3.92 (br d, 1H), 2.43–2.36 (m, 3H), 2.1–1.9 (m, 2H), 1.79 (m, 1H), 1.71 (s, 3H), 1.6–1.4 (m, 2H), 1.44 (s, 3H), 1.42 (s, 3H), 1.3–1.2 (m, 4H), 0.85 (t, 3H). $^{13}$C NMR ($CDCl_3$) δ ppm 171.56, 142.87, 139.24, 139.08, 128.64, 128.36, 128.31, 126.92, 126.89, 124.93, 115.43, 87.27, 57.53, 45.94, 35.43, 33.46, 31.51, 30.60, 29.96, 24.04, 23.34, 23.20, 23.17, 22.48, 13.97. $R_f$ (20% EtOAc/hexane): 0.48. $[\alpha]_D^{25}=-45.9°$ (c=1.298, $CHCl_3$). Elemental Analysis: 78.69% C, 8.93% H.

EXAMPLE 2a

One-Step Reaction of Monoacetate Compound (8) with Olivetol to Produce $\Delta^9$THC

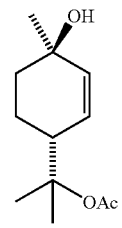

(8)

A 25 ml roundbottom flask with a stir bar was oven-dried, fitted with septa, and cooled under $N_2$. The monoacetate (8) (109 mg) and olivetol (92.5 mg) were added. Anhydrous $CH_2Cl_2$ (8 ml) was added and stirred. The solution was cooled to −5° C. internal temperature. $BF_3 \cdot (OEt)_2$ (65 μl, 1.0 eq.) was added. The solution gradually darkened to orange. After 24 minutes, the reaction was quenched with 10% $Na_2CO_3$. The layers were separated and the aqueous layer was extracted twice with $CH_2Cl_2$. The organics were combined and washed with water and saturated NaCl solution, then dried over $Na_2SO_4$, filtered, and concentrated in vacuo to oil. HPLC showed 64.0 area percent $\Delta^9$-THC. The oil was chromatographed on 20 g TLC mesh silica to yield 58.7 mg (36.3%) of $\Delta^9$-THC. $^1$H NMR agreed with published reports and commercial samples.

EXAMPLE 2b

Reaction of Monoacetate Compound (8) with Olivetol to Produce Ring-Open Intermediate A 25 ml 2-neck roundbottom flask with a stir bar was oven-dried, fitted with septa, and cooled under $N_2$. The monoacetate (8) (109 mg, 0.514 mmol) and olivetol (92.5 mg) were added. Anhydrous $CH_2Cl_2$ (8 ml) was added. The solution was stirred to dissolve the solids and then cooled to −20° C. internal temperature. $BF_3 \cdot (OEt)_2$ (16 μl, 0.25 eq.) was added. The solution was stirred for 45 minutes and then quenched with 10% $Na_2CO_3$ (aq.) (4 ml). The mixture was extracted twice with $CH_2Cl_2$. The combined organics were washed with water, dried over $Na_2SO_4$, filtered, and concentrated in vacuo to a colourless oil. Chromatography on silica gel yielded 90.5 mg (47.0% yield) of acetyl triol (the ring open product corresponding to compound D). $^1$H NMR ($CDCl_3$): δ (ppm) 6.22 (br m, 2H,), 5.76 (br s, 2H), 5.36 (s, 1H), 4.00 (br d, 1H), 2.67 (dt, 1H), 2.40 (t, 2H), 2.26–2.16 (m, 1H), 2.07–1.90 (m, 2H), 1.73 (s, 3H), 1.51 (s, 3H), 1.49 (s, 3H), 1.42 (s, 3H), 1.32–1.24 (m, 41H), 0.85 (t, 3H). $^{13}$C NMR ($CDCl_3$): δ (ppm) 170.83, 142.69, 138.03, 124.99, 115.42, 85.90, 44.29, 35.38, 33.47, 31.49, 30.66, 30.09, 25.16, 24.65, 23.17, 22.57, 22.43, 21.84, 13.95. $R_f$ (20% EtOAc/hexane): 0.37.

EXAMPLE 3a

One-Step Reaction of Monomethoxy Compound (9) with Olivetol to Produce Δ⁹-THC

A 25 ml roundbottom flask with a stir bar was oven-dried, fitted with septa, and

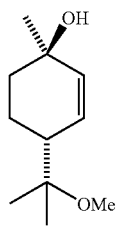

(9)

cooled under $N_2$. The monomethoxy compound (9) (91.9 mg) and olivetol (90 mg) were added. Anhydrous $CH_2Cl_2$ (8 ml) was added and stirred. The solution was cooled to −5° C. internal temperature. $BF_3.(OEt)_2$ (16 μl, 0.25 eq.) was added. After 1 hour another 16 μl was added. Two hours later, another 32 μl was added. The solution gradually darkened to orange. TLC showed a mixture of Δ⁹-THC and the ring open product, and major spots. The reaction was quenched with 10% $Na_2CO_3$. The layers were separated and the organic was washed with water and sat. NaCl, then dried over $Na_2SO_4$, filtered, and concentrated in vacuo to oil.

EXAMPLE 3b

Reaction of Monomethoxy Compound with Olivetol to Produce Ring-Open Intermediate A 5 ml roundbottom flask with a stir bar was oven-dried, fitted with a septum, and cooled under $N_2$. The monomethoxy compound (9) (33.5 mg) in 1.5 ml of anhydrous methylene chloride was added. Olivetol (32.7 mg) and magnesium sulfate (134 mg) were added. p-Toluenesulfonic acid monohydrate (34.6 mg) was added. The slurry was stirred at room temperature for 30 minutes. Solid $NaHCO_3$ (100 mg) was added and stirred. The solids were removed by filtration. The solution was washed once with 5% $NaHCO_3$ (aq.). The aqueous wash was extracted once with $CH_2Cl_2$. The organics were combined, washed with water, and dried over $Na_2SO_4$. The solution was concentrated in vacuo and chromatographed on silica gel. Colourless oil of the methoxy triol (the ring open product corresponding to compound D) (35.3 mg, 56.0% yield) was obtained. $^1H$ NMR ($CDCl_3$): δ (ppm) 7.90 (br s, 1H), 6.68 (br s, 1H), 6.33–6.21 (br d, 2H) 5.75 (s, 1H), 3.74 (s, 1H), 3.20 (s, 3H), 2.44 (t, 2H), 2.07 (br s, 2H), 2.00–1.77 (m, 3H), 1.80 (s, 3H), 1.54 (m, 2H), 1.31 (m, 3H), 1.14 (s, 3H, 1.13 (s, 3H), 0.87 (t, 3H). $^{13}C$ NMR ($CDCl_3$): δ (ppm) 186.50, 169.63, 166.85, 143, 41, 140.11, 123.58, 79.32, 48.63, 48.05, 35.51, 32.62, 31.52, 30.63, 27.76, 23.74, 23.01, 22.53, 21.95, 20.39, 13.99. Elemental Analysis: 73.3% C, 8.80% H. $R_f$ (10% EtOAc/hexane): 0.25. $[α]_D^{25}$=−22.70 (c=0.088, $CHCl_3$).

EXAMPLE 4

One-Step Reaction of Diacetate (10) with Olivetol to Produce Δ⁹-THC Preparation of Diacetate (10)

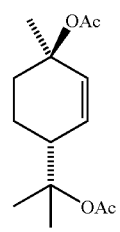

(10)

A 100 ml three-necked roundbottom flask with a stir bar was oven-dried, fitted with septa, and cooled under $N_2$. (+)-p-menth-2-ene-1,8-diol (10.00 g) was added. Triethylamine (68.7 ml, 8.4 eq.) was added and the slurry was stirred. N,N-dimethylaminopyridine (1.435 g, 0.2 eq.) was added. Acetic anhydride (23.3 ml) was placed in an addition funnel and added slowly over 15 minutes. The yellow solution became homogeneous. The solution was warmed to 35° C. internal temperature and stirred for 2.5 hours, then raised to 40° C. for another three hours, then allowed to stir for 13 hours at room temperature. The reaction was quenched with water while cooling in ice. The mixture was extracted three times with hexane and once with ethyl acetate. The organics were combined and washed with saturated NaCl (aq.), dried over $Na_2SO_4$, filtered and concentrated in vacuo to an orange oil. Chromatography on 50 g TLC mesh silica yielded the diacetate (10) as a colourless oil (12.3 g, 82.3%). The oil was cooled in dry ice to freeze the oil and then the solid was broken up with a spatula. It was allowed to warm to room temperature and it remained a white solid. $^1H$ NMR ($CDCl_3$): δ (ppm): 5.84 (dd, 1H), 5.54 (dd, 1H), 2.70 (m, 1H), 2.05–1.8 (m, 3H), 1.85 (s, 6H), 1.68 (m, 1H), 1.40 (s, 3H), 1.30 (s, 3H), 1.29 (s, 3H). $^{13}C$ NMR ($CDCl_3$): δ (ppm) 169.95, 169.89, 132.40, 127.88, 83.79, 79.73, 43.62, 33.85, 25.26, 23.10, 22.74, 22.05, 21.49. m.p. 28–31° C. Elemental Analysis: 65.26% C, 8.61% H. $R_f$ (20% EtOAc/hexane): 0.52. $[α]_D^{25}$=+73.5° (c=0.99, $CHCl_3$).

One-Step Reaction

A 25 ml roundbottom flask with a stir bar was oven-dried, fitted with septa, and cooled under $N_2$. The diacetate (10) (126.9 mg, 0.499 mmol) and olivetol (90 mg, 0.499 mmol) were added. Anhydrous $CH_2Cl_2$ (8 ml) was added and stirred. The solution was cooled to −5° C. internal temperature. $BF_3.(OEt)_2$ (64 μl, 1.0 eq.) was added. The solution gradually darkened to red. After 15 minutes, the reaction was quenched with 10% $Na_2CO_3$. The layers were separated and the organic layer was washed with 10% $Na_2CO_3$. The combined aqueous were extracted once with $CH_2Cl_2$. The organics were combined and washed with water and saturated NaCl solution, then dried over $Na_2SO_4$, filtered, and concentrated in vacuo to a tannish oil (0.132 mg). HPLC showed 88.8 area percent Δ⁹-THC. Chromatography on silica gel yielded 95.9 mg (61.0% yield) of Δ⁹-THC. HPLC showed 94.9 area percent Δ⁹-THC.

EXAMPLE 5

One-Step Reaction of Dibenzoate (11) with Olivetol to Produce Δ$^9$-THC Preparation of Dibenzoate (11)

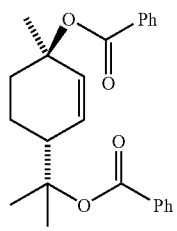

(11)

A 25 ml three-necked roundbottom flask with a stir bar was oven-dried, fitted with septa, and cooled under $N_2$. (+)-p-Menth-2-ene-1,8-diol (1.00 g) was added. Pyridine (6 ml, 12.6 eq.) was added and the pale yellow solution was stirred. N,N-dimethylaminopyridine (0.1435 g, 0.2 eq.) was added. Benzoyl chloride (2.73 ml, 4 eq.) was added. After 10 minutes, a solid precipitated. The slurry was allowed to stir overnight at room temperature. The reaction was quenched with water. The mixture was extracted three times with $CH_2Cl_2$. The organics were combined and washed with water and saturated NaCl (aq.), dried over $Na_2SO_4$, filtered and concentrated in vacuo. The oil was chromatographed on 25 g TLC mesh silica to yield a colourless oil. The oil was cooled in dry ice and froze, but melted on warming to room temperature. $^1$H NMR(CDCl$_3$) δ (ppm): 8.0 (dt, 4H), 7.51 (m, 2H), 7.40 (dt, 4H), 6.16 (dd, 1H), 5.88 (dd, 1H), 3.00 (m, 1H), 2.29 (m, 2H), 2.02 (m, 1H), 1.70 (s, 3H), 1.62 (s, 314), 1.60 (s, 3H), 1.25 (m, 1H). $^{13}$C NMR (CDCl$_3$) δ (ppm): 165.53, 132.80, 132.53, 132.50, 131.77, 131.63, 129.40, 129.36, 128.39, 128.22, 128.16, 80.64, 44.55, 34.09, 25.81, 23.50, 23.10, 22.59, 21.99, 14.14, 14.05. Elemental Analysis: 76.21% C, 6.97% H. R$_f$ (20% EtOAc/hexane): 0.57.

On-Step Reaction

A 25 ml roundbottom flask with a stir bar was oven-dried, fitted with septa, and cooled under $N_2$. The dibenzoate (11) (189 mg, 0.499 mmol) and olivetol (90 mg) were added. Anhydrous $CH_2Cl_2$ (8 ml) was added and stirred. The solution was cooled to −5° C. internal temperature. BF$_3$·(OEt)$_2$ (64 μl, 1.0 eq.) was added. The solution gradually darkened to red. After 15 minutes, the reaction was quenched with 10% $Na_2CO_3$. The layers were separated and the organic layer was washed with water and saturated NaCl solution, then dried over $Na_2SO_4$, filtered, and concentrated in vacuo to oil. HPLC showed 78.8 area percent Δ$^9$-THC.

EXAMPLE 6

One-Step Reaction of di-p-nitrobenzoate (12) with Olivetol to Produce Δ$^9$-THC Preparation of di-p-nitrobenzoate (12)

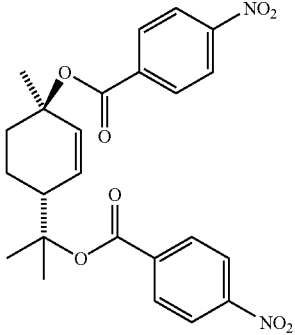

(12)

A 25 ml three-necked roundbottom flask with a stir bar was oven-dried, fitted with septa, and cooled under $N_2$. (+)-p-Menth-2-ene-1,8-diol (1.00 g) was added. Pyridine (6 ml, 12.6 eq.) was added and the pale yellow solution was stirred. N,N-dimethylaminopyridine (0.1435 g, 0.2 eq.) was added. p-Nitrobenzoyl chloride (4.58 ml, 4.2 eq.) was added. After a few minutes, tan solid precipitated. More pyridine (12 ml) was added. The slurry was allowed to stir overnight at room temperature. The reaction was quenched with water. The mixture was extracted three times with ethyl acetate. The organics were combined and washed twice with saturated NaCl (aq.), dried over $Na_2SO_4$, filtered and concentrated in vacuo to light yellow solid. The solid was recystallized from isopropyl alcohol and dried under vacuum. The yield was 3.303 g (120% yield), which clearly still contained pyridine and isopropyl alcohol by NMR. It was dried more and then recrystallized from ethyl acetate/hexane to give a lightly coloured solid (1.89 g, 68.7%). $^1$H NMR (d$_6$-acetone) still seemed to have too many aryl protons. $^1$H NMR (CD$_2$Cl$_2$) δ (ppm): 8.3–8.2 (m, 4H), 8.2–8.1 (m, 4H), 6.14 (dd, 1H), 5.88 (d, 1H), 3.04 (m, 1H), 2.29 (m, 2H), 2.00 (m, 1H), 1.70 (s, 3H), 1.62 (s, 3H), 1.60 (s, 3H0, 1.67–1.65 (m, 2H). $^3$C NMR (CD$_2$Cl$_2$) δ (ppm): 164.275, 164.244, 151.00, 133.00, 131.46, 131.09, 131.04, 129.29, 124.00, 123.96, 87.04, 82.75, 45.00, 34.55, 26.10, 23.83, 23.45, 22.64. m.p>200° C. (decomposition). Elemental Analysis: 59.68% C, 4.71% H, 6.07% N. Rf (20% EtOAc/hexane): 0.41. [α]$_D^{25}$=+38.0° (c=0.21, CHCl$_3$).

One-Step Reaction

A 10 ml roundbottom flask with a stir bar was oven-dried, fitted with septa, and cooled under $N_2$. The di-p-nitrobenzoate (12) (116.5 mg) and olivetol (45 mg) were added. Anhydrous $CH_2Cl_2$ (4 ml) was added and stirred. The solution was cooled to −5° C. internal temperature. BF$_3$·(OEt)$_2$ (32 μl, 1.0 eq.) was added. The cloudy solution gradually darkened to orange. After 2 hours, the reaction was quenched with 10% $Na_2CO_3$. The layers were separated and the organic layer was washed with water and sat. NaCl, then dried over $Na_2SO_4$, filtered, and concentrated in vacuo to yellow oil. HPLC showed 71.5 area percent Δ$^9$-THC.

The invention claimed is:
1. A process for the production of a compound of general formula A:

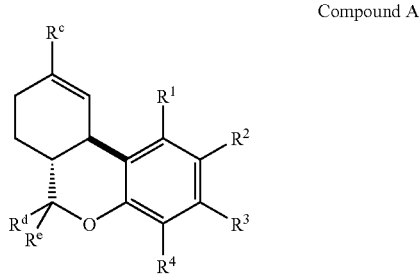

Compound A wherein $R^c$, $R^d$ and $R^e$ are independently H, alkyl, or substituted alkyl; and $R^1$ to $R^4$ are independently H, OH, OR' (R' is alkyl, aryl, substituted alkyl or aryl, silyl, acyl, or phosphonate), alkyl, substituted alkyl, aryl, acyl, halide, amine, nitrate, sulphonate or phosphonate;
comprising reacting compound B with compound C:

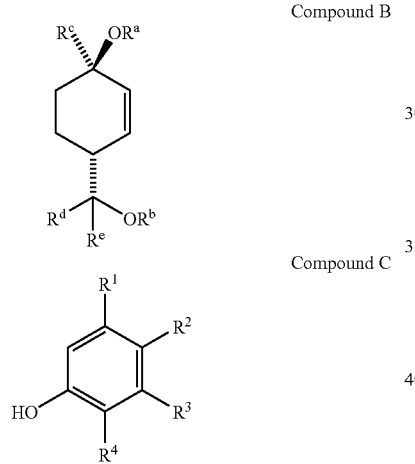

Compound B

Compound C wherein $R^a$ is H, alkyl, aryl, acyl or silyl; $R^b$ is alkyl, aryl or acyl; $R^c$, $R^d$, $R^e$ and $R^1$ to $R^4$ are as hereinbefore defined.

2. A process according to claim 1, wherein $R^a$ is alkyl, aryl or acyl.
3. A process according to claim 1, wherein $R^b$ is an acyl group.
4. A process according to claim 3, wherein $OR^b$ is an ester group selected from the group consisting of acetate, propionate, butyrate, trimethylacetate, phenylacetate, phenoxyacetate, diphenylacetate, benzoate, p-nitrobenzoate, phthalate and succinate.
5. A process according to claim 1, wherein both $R^a$ and $R^b$ are acyl groups.

6. A process according to claim 5, wherein $OR^a$ and $OR^b$ are ester groups independently selected from the group consisting of acetate, propionate, butyrate, trimethylacetate, phenylacetate, phenoxyacetate, diphenylacetate, benzoate, p-nitrobenzoate, phthalate and succinate.
7. A process according to claim 6, wherein $OR^a$ and $OR^b$ are diphenylacetate.
8. A process according to claim 1 wherein $R^c$, $R^d$ and $R^e$ are methyl.
9. A process according to claim 1, wherein $R^1$ is OR" wherein R" is H, alkyl, substituted alkyl, acyl or silyl.
10. A process according to claim 9, wherein $R^1$ is OH.
11. A process according to claim 1, wherein $R^2$ and $R^4$ are H.
12. A process according to claim 1, wherein $R^3$ is $C_5H_{11}$.
13. A process according claim 1, wherein compound A is $\Delta^9$-THC, compound B is an ether or ester of (+)-p-menth-2-ene-1,8-diol and compound C is olivetol.
14. A process according to claim 1, wherein the reaction of compound B with compound C is carried out in the presence of an acid catalyst.
15. A process according to claim 14, wherein the acid catalyst is nonmetallic.
16. A process according to claim 14, wherein 0.1–1.5 equivalents of acid catalyst are used.
17. A compound, represented by structure B,

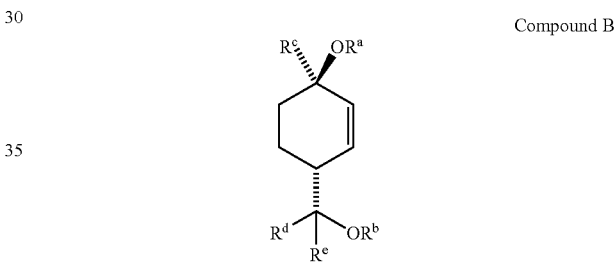

Compound B wherein $OR^a$ and $OR^b$ are independently chosen from acetate, propionate, butyrate, trimethylacetate, phenylacetate, phenoxyacetate, diphenylacetate, benzoate, p-nitrobenzoate, phthalate and succinate (provided that only one of $OR^a$ and $OR^b$ is acetate), and $R^c$, $R^d$ and $R^e$ are independently H, alkyl, or substituted alkyl.
18. A compound according to claim 17, wherein $OR^a$ and $OR^b$ are diphenylacetate.
19. A process according to claim 1 further comprising performing a ring closure step.
20. A process according to claim 8, wherein $R^1$ is OH, $R^2$ and $R^4$ are H, and $R^3$ is $C_5H_{11}$.
21. A process according to claim 6, wherein no more than one of $OR^a$ and $OR^b$ is acetate.

* * * * *